US010663375B2

(12) United States Patent
Gaeckle et al.

(10) Patent No.: US 10,663,375 B2
(45) Date of Patent: May 26, 2020

(54) MEDICAL CUTTING DEVICE COMPRISING A ROTATING KNIFE (71) Applicant: Heinz Kurz GmbH, Dusslingen (DE)

(72) Inventors: Markus Gaeckle, Bad Liebenzell (DE); Axel Lang, Reutlingen (DE)

(73) Assignee: Heinz Kurz GmbH, Dusslingen (DE)

( * ) Notice: Subject to any disclaimer, the term of this patent is extended or adjusted under 35 U.S.C. 154(b) by 119 days.

(21) Appl. No.: 15/926,270

(22) Filed: Mar. 20, 2018

(65) Prior Publication Data
US 2018/0340867 A1 Nov. 29, 2018

(30) Foreign Application Priority Data

May 29, 2017 (DE) .................... 10 2017 111 634

(51) Int. Cl.
| *G01N 1/00* | (2006.01) |
| *G01N 1/06* | (2006.01) |
| *B26D 7/02* | (2006.01) |
| *B26D 1/143* | (2006.01) |
| *B26D 3/28* | (2006.01) |

(Continued)

(52) U.S. Cl.
CPC .......... *G01N 1/06* (2013.01); *A61B 17/1635* (2013.01); *A61F 2/30756* (2013.01); *A61F 2/4644* (2013.01); *B26D 1/143* (2013.01); *B26D 1/26* (2013.01); *B26D 3/28* (2013.01); *B26D 5/08* (2013.01); *B26D 5/086* (2013.01); *B26D 7/02* (2013.01); *A61B 17/1679* (2013.01); *A61B 17/1688* (2013.01); *A61B 2017/00787* (2013.01); *A61B 2017/00792* (2013.01); *A61B 2017/00969* (2013.01); *A61F 11/004* (2013.01);

(Continued)

(58) Field of Classification Search
CPC ........................................................ G01N 1/00
See application file for complete search history.

(56) References Cited

U.S. PATENT DOCUMENTS

2010/0286693 A1   11/2010   Steinhardt et al.

FOREIGN PATENT DOCUMENTS

| DE | 102013105857 | 12/2014 |
| EP | 0483567 | 5/1992 |
| WO | WO 99/51962 | * 10/1999 |

OTHER PUBLICATIONS

European Search Report dated Sep. 13, 2018 in European Application No. 18 15 7323 with English translation of the relevant parts.

* cited by examiner

*Primary Examiner* — Jyoti Nagpaul
(74) *Attorney, Agent, or Firm* — Collard & Roe, P.C.

(57) ABSTRACT

A medical cutting device for creating thin slices, has a device body, a cover, a working section which rigidly adjoins a connecting section, and a recess on the top side, which is enclosed by a delimiting ridge. The cover comprises a counterpart to the connecting section adjoined by a pressure section which is positioned opposite the recess at a distance $d_a$, and therefore a guide slot extending between the working section and the pressure section remains free for a cutting blade. The distance of the guide slot to the bottom surface of the recess, which is defined by the distance $d_a$, defines the thickness, which can be achieved, of a slice to be created. The cutting blade is disposed within the guide slot and is rigidly connected to a rotatable shaft extending perpendicularly to the plane of the guide slot and extends through a recess in the cover.

17 Claims, 7 Drawing Sheets (51) Int. Cl.
  *A61B 17/16* (2006.01)
  *B26D 1/26* (2006.01)
  *B26D 5/08* (2006.01)
  *A61F 2/30* (2006.01)
  *A61F 2/46* (2006.01)
  *A61B 17/00* (2006.01)
  *A61F 11/00* (2006.01)
(52) U.S. Cl.
  CPC .............. *A61F 2002/3096* (2013.01); *G01N 2001/061* (2013.01); *G01N 2001/065* (2013.01)

MEDICAL CUTTING DEVICE COMPRISING A ROTATING KNIFE

CROSS REFERENCE TO RELATED APPLICATIONS

This application claims priority under 35 USC 119 of German Patent Application No. 10 2017 111 634.6 filed on May 29, 2017, the disclosure of which is herein incorporated by reference.

BACKGROUND OF THE INVENTION

The invention relates to a medical cutting device for creating thin tissue or cartilage slices, comprising a device body and a cover, wherein a first holding device is provided, which includes a first working section comprising a first recess which is located on the top side of the device body, the recess being entirely or partially enclosed by a first limiting ridge. The device body comprises a connecting section which is directly, rigidly adjoined by the first working section. The cover comprises a counterpart to the connecting section which is directly, rigidly adjoined by a first pressure section. In the operating state of the cutting device, the first pressure section is disposed opposite the first recess in the first working section at an essentially uniform first distance $d_a$ defined by the geometric shape of the connecting section and the counterpart thereof, and therefore a guide slot extending between the first working section and the first pressure section remains free for a cutting blade. The distance of the guide slot to the bottom surface of the first recess, which is defined by the distance $d_a$ defines the thickness, which can be achieved with the aid of the first holding device, of a slice to be created by means of the cutting device.

A device of this type is known from DE 10 2013 105 856 B4.

Time and time again, it becomes necessary for various medical purposes to cut a piece of thin, endogeneous tissue, in particular cartilage slices having uniform thicknesses, out of a larger piece of cartilage which has been removed, for example, from the auricle, the tragus, the cartilaginous portion of the upper bony rib, or the nasal septum. For example, it can be necessary to examine special properties of the main body in greater detail, in particular under a microscope. In otorhinolaryngology, thin cartilage slices of this type are also required in many surgical applications, such as in the middle ear region to cover a middle ear prosthesis, to restore the posterior wall of the auditory meatus, or for the plastic repair of a defect of the tympanic membrane. Thin cartilage slices of this type are also used in many nasal surgeries, in order to perform functional or aesthetic corrections of the nose.

A cutting device is described in EP 0 483 567 B1, with the aid of which thin cartilage slices, which have a thickness which is predefinable within certain limits, can foe cut out of a larger piece of cartilage quickly, reliably, and with a consistent level of quality. In order to obtain different thicknesses of the cartilage slices that are created, however, special shims having a known thickness must be placed in the cutting device. These shims, similar to the cutting device itself, must be thoroughly cleaned and kept sterile, and they must be handled separately in this manner before every operation, which is a time-consuming process that is susceptible to error. Considering that an average ENT hospital has three to four surgical suites, and, at peak times, fifteen to twenty patients may be operated on in one day, it is possible that a cartilage cutter must be made available up to fifteen times a day. This poses a great logistical challenge in terms of supplying sterilized materials. Moreover, handling the shims is not entirely easy. For example, due to the small size of the shims, it is not always possible to label them adequately and in an easily recognized manner, even though this is necessary in order to ensure that precisely the proper shim having the particular size that is required is available during the operation. In addition, special skills are required to insert the relatively small shims into the cutting device correctly, and to fix them in position therein.

In order to ensure that thin cartilage slices having certain different thicknesses can be created in a consistent level of quality, even without using the known shims, it is provided according to US 2010/0236693 A1—as is also the case with the known cutting device according to EP 0 483 567 B1—that the first recess, which is disposed in the first working section on the top side of the device body, is closable via a first projection disposed on the top side of the cover, wherein the first lateral limiting ridge comprises a first guide slot for the insertion of a cutting blade, the guide slot extending from an end face of the first section at a predefined first distance in parallel to the bottom surface of the first recess. In addition, in the device according to US 2010/0286693 A1, at least one second holding device is to be provided, which comprises a second section including a second recess which is disposed on the top side of the device body and is entirely or partially enclosed by a second limiting ridge and is closable via a second projection which is disposed on the top side of the cover, wherein the second lateral limiting ridge comprises a second guide slot for the insertion of a cutting blade, the guide slot extending from an end face of the second section at a predetermined, second distance in parallel to the bottom surface of the second recess.

Since different distances between the particular guide slot and the corresponding bottom surface of the particular recess can foe selected for different holding devices, cartilage slices having certain different thicknesses can be created with the aid of this known cutting device including the different holding devices, without the need to use the shims which are indispensible in the previous prior art. In addition, a handling of this cutting device between the thumb and the index finger provides the operating surgeon with greater confidence during the actual cutting procedure, because all parts—due to the geometry and the design thereof—can be moved relative to each other in a reliable and controlled manner. The disadvantage of this known cutting device, however, is that the production of parts is highly complex. Products produced using injection-molding technology in particular have the characteristic that considerable problems can result when walls are very thin. As a consequence thereof, the products generally cannot be produced cost-effectively, due to the financial outlay involved.

DE 10 2013 105 857 B4 cited at the outset improves this prior art, in that it provides a modified cutting device—which is generic for the present invention—having the features defined at the outset. When this improved device is utilized, however, there is also a certain risk of injury for the person handling the device, because the cutting blade, before being inserted into the guide slot, is freely accessible and, therefore, can cut the user in the finger if a clumsy movement is carried out. Yet another disadvantage of this known device (as well as of the above-discussed prior art) is that the knife for cutting off the desired cartilage slice must be handled using sawing or chopping motions, which often results in non-uniform cutting results. In addition, the cutting procedure cannot be automated in any of the known devices, but rather absolutely must always be carried out manually.

SUMMARY OF THE INVENTION

By contrast, it is an object of the present invention to improve the generic medical cutting device of the type described at the outset in a simple and cost-affective manner using the simplest possible technical means in such a way that the above-described advantages of the known cutting devices are retained to the greatest possible extent, but the aforementioned disadvantages are avoided. In particular, it is to be ensured by way of the invention that the cutting procedure can be carried out easily and safely, wherein particularly uniform cutting results which yield high-quality cut products are to be obtainable, and wherein the cutting device is to offer the possibility for carrying out the cutting procedure in an automated manner.

This relatively complex problem is solved according to the invention in a way which is as surprisingly simple as it is effective, in that, in a medical cutting device of the type in question, the cutting blade is disposed within the guide slot and is rigidly connected to a rotatable shaft which is mounted so as to be rotatable about an axis of rotation extending perpendicularly to the plane of the guide slot and extends through a recess in the cover, perpendicularly to the plane of the guide slot.

Due to this design and the mode of operation predefined thereby, it can be ensured that the sharp cutting blade always remains hidden, on all sides within the guide slot, during use, and so there is no risk of injury for an operator.

In contrast to the above-described devices according to the prior art, due to the rotation of the cutting blade, greatly improved working results are made possible with respect to particularly uniform cuts of the tissue or cartilage piece. In addition, a blade which is rotating, in contrast to a blade which can be simply inserted or pressed in, opens up the possibility of coupling an introduction of force from a motorized (generally mechanical or electrical) power source to the rotatable shaft, in order to therefore design the cutting procedure to be automatable, which ultimately results in even better, finer, and more uniform cutting results.

Particular advantages of the devices according to the invention over the prior art are:
Simplicity: The tissue placed into the recess is held in a positive fit in the cavity during the cut.
Precision: The rotating blade which, due to the rotation of the shaft, effectuates a cutting motion and an advancing of the cutting depth, permits a cut through the tissue held in the recess, which is distinguished, in particular, by a uniform cutting thickness and surface quality.
Safety: The blade is not directly accessible for the user and, therefore, a laceration is impossible.

Very particularly preferred is a class of embodiments of the cutting device according to the invention, in which a hold-down device is available, by means of which, in the operating state of the cutting device, tissue or cartilage material can be pressed onto the bottom surface of the first recess in order to create thin slices. If the tissue is unstable, it can be held in the recess (cavity) by means of the hold-down device and, therefore, can be held in position, again in a positive-fit manner, during the cutting procedure.

One refinement of these embodiments, which can be manufactured very easily in terms of production engineering, is that the hold-down device comprises a mechanical height limitation. As a result, it can be ensured that, on the one hand, the blade edge does not cut into the hold-down device and, therefore, no foreign substances are worn off and enter the graft and, on the other hand, it is additionally made possible, as a result, to produce a defined cutting thickness.

In a simply designed refinement of the aforementioned class of embodiments, in the operating state of the cutting device, the hold-down device can be manually pressed onto the tissue or cartilage material in order to create thin slices. Due to the "manual holding-down", the contact pressure can be applied onto the particular individual tissue consistency. Experienced surgeons/users frequently want to be able to exert influence in specific, manual ways that deviate from the standard.

Alternatively, in the operating state of the cutting device, the hold-down device can also be automatically pressed onto the tissue or cartilage material, by means of spring force, in order to create thin slices. This is advantageous, since a certain standard in the cutting quality and cutting thickness, which is also dependent on the contact pressure, can be created as a result.

Yet another class of embodiments of the cutting device according to the invention, which are particularly easy to produce, is distinguished by the axis of rotation of the rotatable shaft being disposed in the cutting device in a stationary manner. Simplicity and precision, in particular, are advantageous here: Rotating the axis of rotation causes the blade to rotate (cutting motion—"salaam cut") and simultaneously advances the cutting depth. This provides for a highly uniform cutting thickness and surface quality.

In one alternative class of mechanically somewhat more complex embodiments, the axis of rotation of the rotatable shaft is disposed so as to be displaceable in the plane of the guide slot.

Simpler refinements, in turn, are useful for this purpose, in the case of which the axis of rotation of the rotatable shaft is disposed to as to be linearly displaceable in the plane of the guide slot.

By contrast, a class of refinements which is somewhat more complex but can be designed in a considerably more highly variable manner is distinguished by the fact that the axis of rotation of the rotatable shaft is disposed so as to be displaceable on a curved path, preferably on a circular-path section, in the plane of the guide slot. As a result, multiple cavities/recesses can be disposed in a space-saving manner in such a way that the product shape can be ergonomically designed and the cavities are disposed in a certain orientation and, therefore, the tissue is presented to the cutting edge in an optimal way.

Particularly preferred are variants of the above-described refinements, which are distinguished by the fact that the rotatable shaft comprises a pinion which at least partially extends into the guide slot and, in the operating state of the cutting device, engages into a rack disposed in the connecting section. The simplicity of operation, the uncomplicated manufacture, and a perfect combination between rotation (cutting speed) and advance (advancing of the cutting depth) are also advantageous in this case.

Embodiments of the cutting device according to the invention are also advantageous in which a rotary knob is rigidly connected, outside the cover, to the rotatable shaft at the end of the rotatable shaft facing away from the cutting blade. Particular emphasis is placed on the high level of user comfort and the long lever for ensuring good torque for cutting and advancing.

In embodiments of the invention which also offer a particularly great practical advantage, an engagement part for the motorized drive of the rotatable shaft is rigidly connected, outside the cover, to the shaft at the end of the rotatable shaft facing away from the cutting blade. Therefore, in particular, the cutting procedure can be mechanized and even automated. This yields, in particular, a very high level of uniformity of the cut and, therefore, in turn, increased precision and a high surface quality.

The rotatable cutting blade of the cutting device according to the invention can have highly different geometric shapes in numerous embodiments. For example, depending on the special intended use, the cutting blade can have a form which is oval or crescent-shaped or bar-like or circular, in particular on a circular segment, preferably on a quarter circle or semicircle. The blade can have a single-sided or two-sided ground surface and can comprise a straight cutting edge, or even a curved cutting edge. Depending on the type or tissue, the tissue consistency, and the intended precision, an optimally suitable blade shape can be utilized.

Very particularly preferred is a class of embodiments of the cutting device according to the invention, in which the holding device comprises not only one single recess, but also a plurality of recesses which, in the operating state of the cutting device, are disposed under the guide slot. Therefore, several different cutting thicknesses, i.e., tissue slice thicknesses, are made possible with the aid of one single device, without the need to switch the device or a part of the device.

In refinements of these embodiments, the recesses can have highly different geometric designs, in particular with respect to their particular depth and/or with respect, to their particular bottom surface in terms of shape and/or surface area and/or concave, flat, or convex design and/or with respect to their particular limiting ridge in terms of shape and/or size. Therefore, cut products having completely different shapes can then be created in different size classes. Tissue slices having a defined 3D shape can be cheated easily and quickly in this way. This has not been previously possible in this way.

In somewhat more complex embodiment of the cutting device according to the invention, which are particularly suitable for simultaneously processing a plurality of cut products, the connecting section is adjoined, opposite the first working section, by at least one second working section, in particular also a third working section, each including the same shared guide slot, wherein each working section comprises at least one recess, and wherein the recesses are disposed on a line or on a curved line in a plane extending in parallel to the plane of the guide slot.

Depending on the special intended use, the components of the cutting device according to the invention can be designed in highly different geometric configurations. For example, the limiting ridge can have a cross-section which is circular or oval or polygonal, in particular square, in a plane extending in parallel to the plane of the guide slot. In particular, certain pre-prepared tissue sections can therefore be better held in a dimension-ally stable manner.

In one class of embodiments of the cutting device according to the invention, the device body and the cover are detachably connected to each other in the operating state of the cutting device. In this way, a reusable device could also be manufactured, which can be cleaned and disinfected in the disassembled state.

Alternatively, however, in one alternative class of particularly easily handled embodiments, the device body and the cover are non-detachably connected to each other in the operating state of the cutting device, in particular being welded, adhesively bonded, or permanently clamped together. Of particular advantage in this case is the safety for the user, since the user does not need to install sharp blades and, therefore, there is no risk of a laceration. An increased level of safety for the patient results in this ease due to a sterile disposable device. Therefore, there is no risk of contamination due, for example, to insufficient cleaning and sterilization by the user, With respect, to the material selection, there are hardly any limits placed on the cutting device according to the invention, in preferred embodiments, the device body and the cover are made of plastic or metal and the rotating cutting blade is made of metal, ceramic, or cermet.

Opposite faces of the pressure plates can be roughened, ribbed, or knobbed, in order to prevent slippage of the tissue piece or the cartilage to be processed.

Yet another preferred class of embodiments of the cutting device according to the invention is distinguished by the fact that markings are formed on the working sections of the device body and/or on the corresponding sections of the cover, on which the projections are formed; the markings indicate the distance of the guide slot to the bottom surface of the corresponding recess, which is predefined by the particular distance $d_a$, $d_b$, $d_c$, and therefore indicate the thickness, which can be obtained with the aid of the particular holding device, of the cartilage slice to be created.

In refinements of these embodiments, the markings can include numbers which indicate the particular predefined distance of the guide slot to the bottom surface of the corresponding recess, and therefore indicate the thickness, which can be obtained with the aid of the particular holding device, of the cartilage slice to be created, in the metric system of measurement, in particular in millimeters, or in the imperial system of measurement, in particular in inches.

As an alternative or in addition, the markings can also include graphical representations, in particular scale marks, points, and the like, which indicate the particular predefined distance of the guide slot to the bottom surface of the corresponding recess, and therefore indicate the thickness, which can be obtained with the aid of the particular holding device, of the cartilage slice to be created.

Variants of the above-described embodiments are particularly favorable in terms of handling in which the markings are formed on the top side of the device body, in which the recesses are formed, and/or on the underside of the cover opposite the pressure plate(s).

In yet another ergonomically favorable embodiment of the cutting device according to the invention, convex and/or concave gripping aids are formed on the underside of the device body opposite the recesses, and/or on the underside of the cover opposite the cover plates, which are used for orientation, purposes in order to apply a pressure to the particular center of the projections.

In embodiments of the invention, an enclosing border that extends along the edge can be provided on the underside of the cover opposite the pressure plates.

Likewise, in further embodiments, an enclosing wall can be provided on the underside of the device body, which encloses one or multiple working spaces which can be used, for example, for the pretreatment of a cartilage piece before the desired slice is cut off, or for the further processing of the cut-off cartilage slice.

Round and/or oval templates that have different diameters can also be used to process cut-off cartilage slices; in embodiments of the cutting device according to the invention, the templates are incorporated in an area of the cutting device, in particular in one of the working spaces on the underside of the device body opposite the recesses, and/or on the underside of the cover opposite the pressure plates.

Embodiments of the cutting device according to the invention are very particularly advantageous in which a measurement scale is formed in an area of the cutting device, in particular on the underside of the device body opposite the recesses, preferably in a working space, and/or on the underside of the cover opposite the pressure plates, with the aid of which the cartilage pieces to be processed, and/or the cut-off cartilage slices can be easily measured. In this case as well, round or oval templates having different diameters can be incorporated for the detailed processing of the cartilage pieces.

The cutting device according to the invention can also be designed, in particular, as a low-cost disposable product which is discarded after a single use. Therefore, a cleaning and re-sterilization of the device can be avoided. This is becoming more and more important since the contamination of surgical instruments is a continuously growing problem in everyday hospital settings. Therefore, the cutting device according to the invention is very particularly preferably made of a sterilizable plastic. As a result, the cutting device can be manufactured at a considerably lower cost than the typical devices, which are made of metal. The cutting device is then delivered for the operation in a sterile package, and the cutting device can simply be discarded after use. Such a sterile-packaged, disposable product also has the advantage that it is not necessary to perform time-consuming cleaning and sterilization of the cutting device before every operation, and the risk of infection is also minimized, in contrast to the case in which sterilized materials are supplied, in which the risk of infection cannot be ruled out. The cutting device is preferably manufactured in an injection molding process.

BRIEF DESCRIPTION OF THE DRAWINGS

Further features and advantages of the invention will become apparent from the detailed description of exemplary embodiments of the invention which follows, with reference to the figures in the drawing, which shows the details that are essential to the invention. Further features and advantages of the invention will also become apparent from the claims.

The individual features can be implemented individually, or they can be combined in any possible manner to form variants of the invention. The embodiments that are shown and described are not intended to be a conclusive list, but rather serve as examples for the purpose of explaining the invention.

Exemplary embodiments of the invention are represented in the schematic drawing and are described in greater detail in the description which follows.

In the drawings.

DETAILED DESCRIPTION OF THE PREFERRED EMBODIMENTS

The embodiments of the medical cutting device 10; 20; 30; 40 according to the invention, which is depicted in a schematic, spatial manner in the figures of the drawing, are used for creating thin tissue or cartilage slices from a larger piece of cartilage, and are made of a serializable material, preferably a serializable plastic, in an injection molding process in particular, possibly also being made of metal. These embodiments comprise a device body 11; 21; 31; 41 and a cover 12; 22; 32; 42, wherein a first holding device is provided, which has a first working section 11a' including a first recess 13a; 23a; 33a; 43a which disposed on the top side of the device body 11; 21 and is enclosed by a first limiting ridge 14 in entirety or, alternatively, in embodiments which are not represented in the drawing, only partially in each case by means of several individual ridges. The limiting ridge 14 can have a cross-section which is circular or oval or polygonal, in particular square, in a plane extending in parallel to the plane of the guide slot 17.

In the operating state of the cutting device, the device body 11; 21; 31; 41 and the cover 12; 22; 32; 42 are either detachably connected to each other or are non-detachably welded, adhesively bonded, or permanently clamped together.

The device body 11; 21 comprises a connecting section 19' which is directly, rigidly adjoined by the first working section 11a'. The cover 12; 22; 32; 42 comprises a counterpart 19" to the connecting section 19', which is directly rigidly adjoined by a first pressure section 11a". In the operating state of the cutting device 10; 20; 30; 40, the first pressure section 11a" is disposed opposite the first recess 13a; 23a; 33a; 43a of the first working section 11a' at an essentially uniform first distance $d_a$, which is defined by the geometric shape of the connecting section 19' and its counterpart 19", and therefore a guide slot 17; 27; 37; 47, which extends between the first working section 11a' and the first pressure section 11a", remains free for a cutting blade 18; 28; 38; 43 made of metal, ceramic, or cermet, wherein the distance of the guide slot 17; 27; 37; 47 to the bottom surface of the first recess 13a; 23a; 33a; 43a, which is defined by the distance $d_a$, defines the thickness, which can be achieved with the aid of a first holding device, of a tissue or cartilage slice to be created by means of the cutting device 10; 20; 30; 40.

According to the invention, the cutting devices 10; 20; 30; 40 are characterized in that the cutting blade 18; 28; 38; 48 is disposed within the guide slot 17; 27; 37; 47 and is rigidly connected to a rotatable shaft 15; 25; 35; 45 which is mounted so as to be rotatable about an axis of rotation extending perpendicularly to the plane of the guide slot 17; 27; 37; 47 and extends through a recess in the cover 12; 22; 32; 42 perpendicularly to the plane of the guide slot 17; 27; 37; 47.

In general, in the case of the cutting device 10; 20; 30; 40 according to the invention, a hold-down device 16 is present, by means of which, in the operating state of the cutting device, tissue or cartilage material can be pressed onto the bottom surface of the first recess 12a; 23a; 33a; 43a in order to create thin slices. The hold-down device 16 can comprise a mechanical height limitation (not shown in greater detail in the drawing) and, in the operating state of the cutting device, can be pressed onto the tissue or cartilage material, either manually ox, by means of spring force, automatically, in order to create thin slices.

Figure 4A:
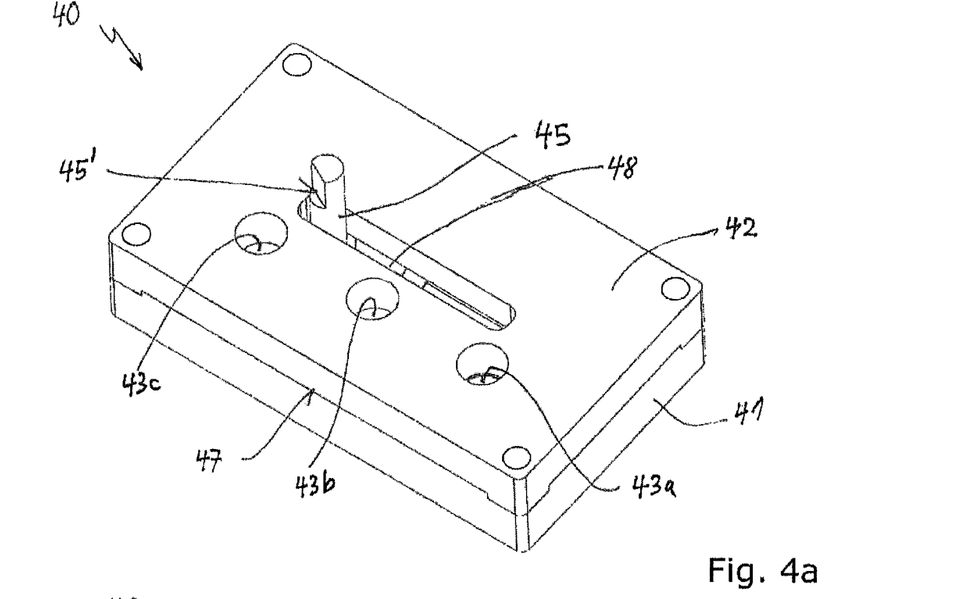
FIG. 4a shows an oblique view of one embodiment comprising three linearly disposed recesses on the device body with the cap placed thereon and comprising a recess as the engagement part for the motorized drive on the upper end of the rotatable shaft.
Figure 4B:
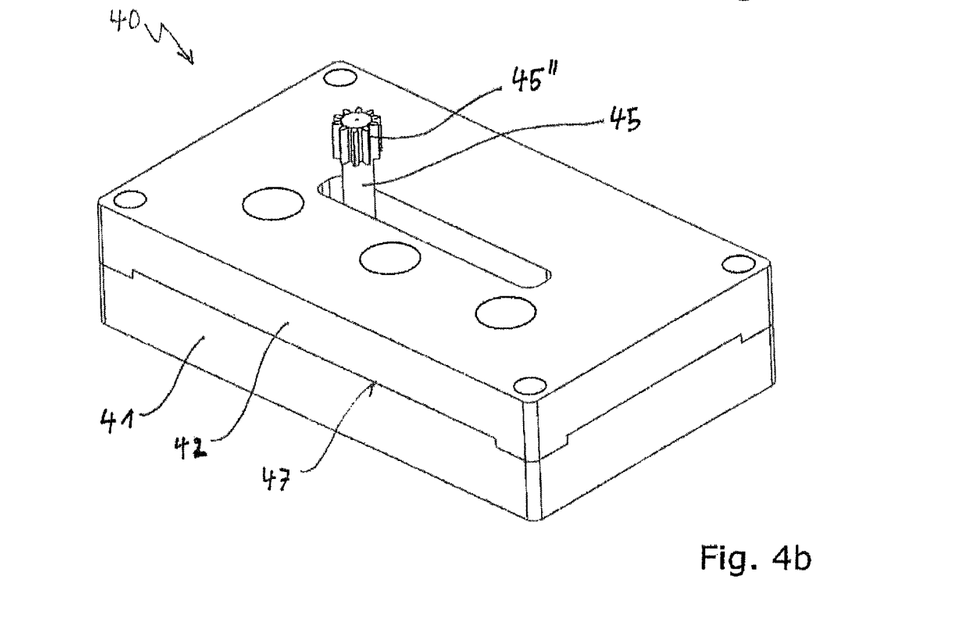
FIG. 4b shows the same as FIG. 4a, although comprising a pinion as the engagement part for a motorized drive at the upper end of the rotatable shaft.

On the end of the rotatable shaft 15; 25; 35 facing away from the cutting blade 18; 28; 38, a rotary knob 15'; 25'; 35' can be rigidly connected to the rotatable shaft 15; 25; 35 outside the cover 12; 22; 32, as represented in FIGS. 1a-c, 2a,b, and 3a-d. FIGS. 4a,b show exemplary embodiments in which an engagement part 45'; 45" for the motorized drive of the rotatable shaft 45 is rigidly connected, outside the cover 42, to the shaft on the end of the rotatable shaft 45 facing away from the cutting blade 48. In FIG. 4a, this engagement part 45' is designed as a step on the upper end of the shaft 45. In particular, the engagement part 45" can also have the shape of a gear or pinion, as represented in FIG. 4b.

FIGS. 1a-c, 3a-d, and 4a,b show embodiments of the cutting device 10; 30; 40 according to the invention, in which, in the operating state of the cutting device, the holding device comprises further recesses 13b; 33b; 43b; 33c; 43c disposed under the guide slot 17; 37; 47 in each case. The recesses can have highly different geometric designs, in particular with respect to their particular depth and/or with respect to their particular bottom surface in terms of shape and/or surface area and/or concave, flat, or convex design and/or with respect to their particular limiting ridge in terms of shape and/or size.

In such embodiments comprising a plurality of recesses 13a; 33a; 43a; 13b; 33b; 43b; 33c; 43c, it is advantageous when the axis of rotation of the rotatable shaft 15; 35; 45 is displaceable in the plane of the guide slot 17; 37; 47, in order to reach all available recesses with only one single cutting blade 18; 38; 48.

In such embodiments comprising a plurality of recesses 13a; 33a; 43a; 13b; 33b; 43b; 33c; 43c, it is advantageous when the axis of rotation of the rotatable shaft 15; 35; 45 is displaceable in the plane of the guide slot 17; 37; 47, in order to reach all available recesses with only one single cutting blade 18; 38; 48.

FIGS. 1a-c, 3a-c and 4a, b show embodiments having a linear displaceability of the rotatable shaft 15; 35; 45. Not specifically shown in the drawing are embodiments of the invention in which the axis of rotation of the rotatable shaft is displaceable on a curved path, approximately on a circular-path section, in the plane of the guide slot.

Figure 1A:
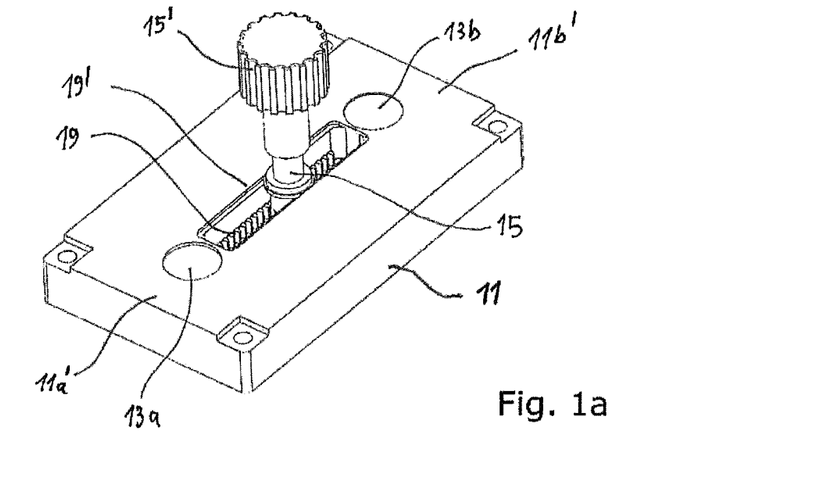
FIG. 1a shows a schematic spatial representation, obliquely, of the top side of the device body of one embodiment of the cutting device according to the invention comprising two recesses and a rack connecting these recesses, and comprising a knurled rotary knob on the upper end of the rotatable shaft.

In the embodiments of the cutting device 10; 30 according to the invention shown in FIGS. 1a, b and 3a-d, a rack 19; 39 disposed in the connecting section 19' is also evident in each case. A pinion which is disposed on the rotatable shaft 15; 35 and at least partially extends into the guide slot 17; 37 can engage into the rack; the pinion is not specifically shown, in the drawing for the sake of clarity.

Figure 2A:
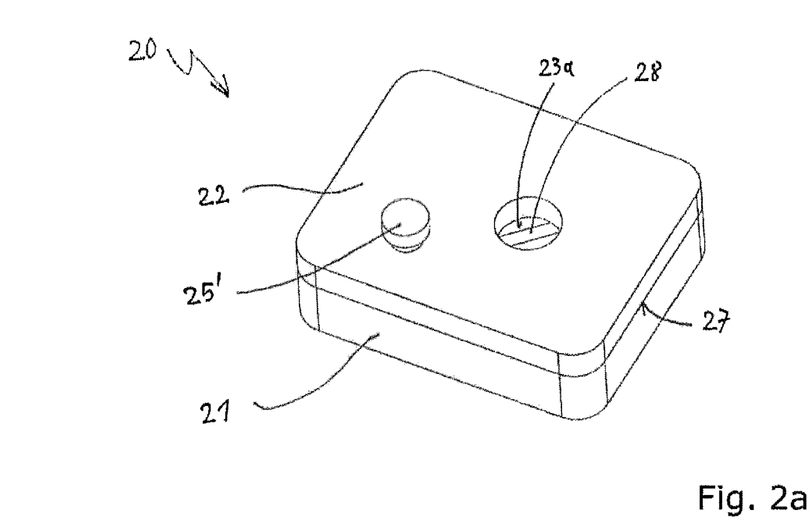
FIG. 2a shows a schematic oblique view of a very simple embodiment comprising a bar-shaped, asymmetrically rotating cutting blade and a single recess.
Figure 2B:
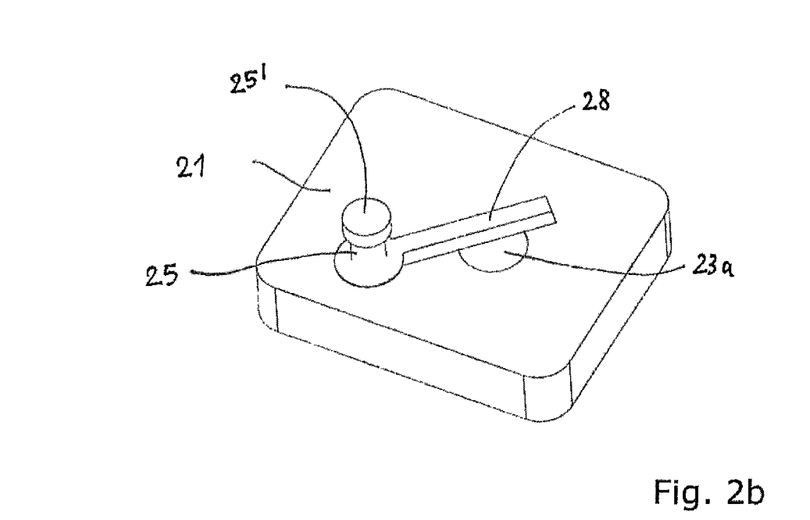
FIG. 2b shows the embodiment from FIG. 2a, although without a cover.
Figure 3A:
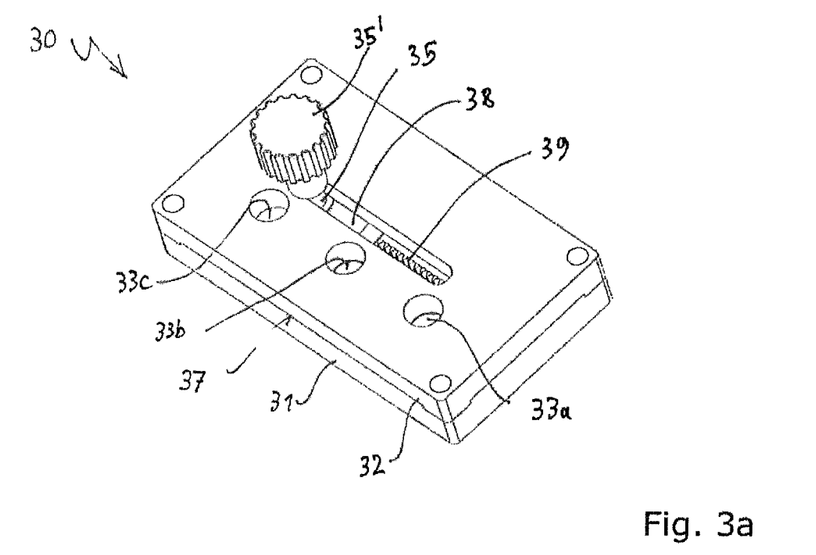
FIG. 3a shows an oblique view of one embodiment comprising a circular cutting blade and three linearly arranged recesses on the device body with the cap placed thereon.
Figure 3B:
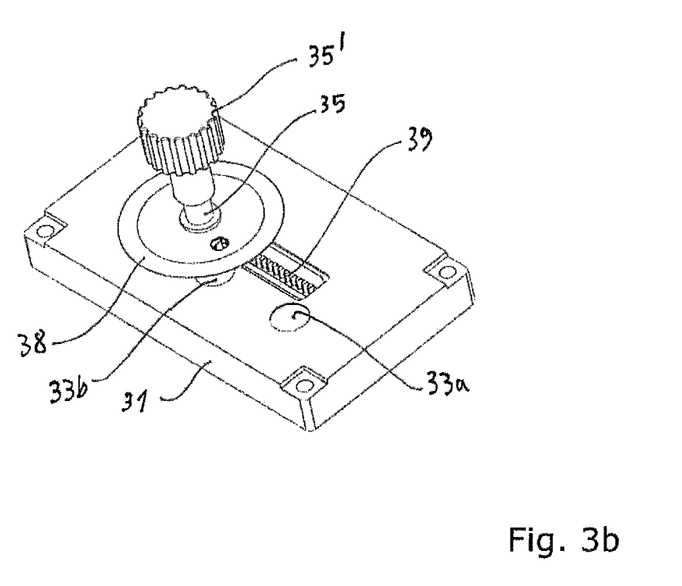
FIG. 3b shows the embodiment from FIG. 3a, with the cover partially removed.
Figure 3C:
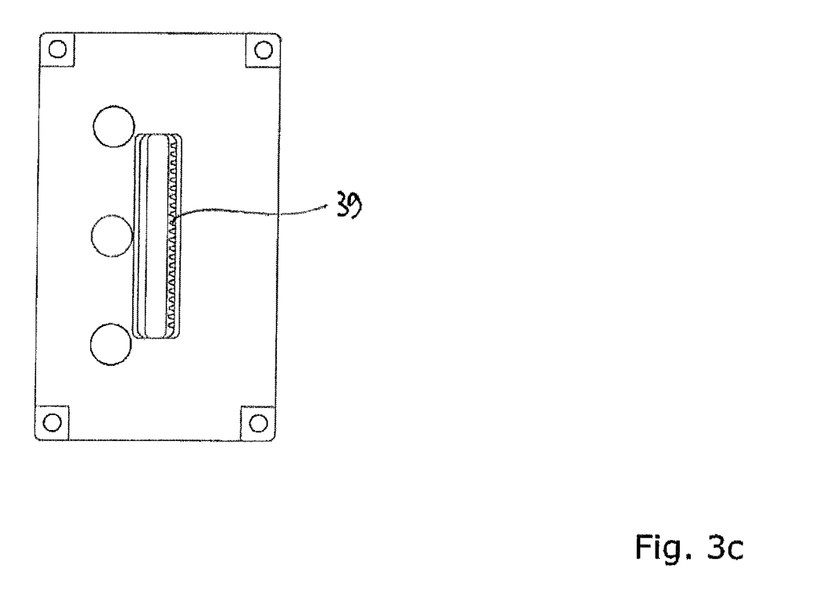
FIG. 3c shows a top view from above of the embodiment from FIG. 3b.
Figure 3D:
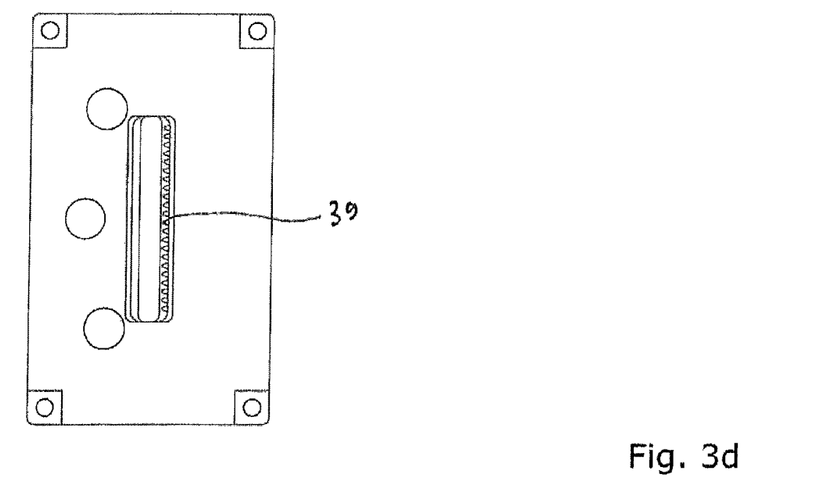
FIG. 3d shows a top view as in FIG. 3c of one embodiment comprising three recesses, which are disposed on a curved line, in the device body.

By contrast, the axis of rotation of the rotatable shaft 25 of the embodiment according to FIGS. 2a,b is fixedly disposed in the cutting device 20. Since only one single recess 23a is available in this very simple embodiment, a displaceability of the shaft 25 would generally not be meaningful.

In addition to the first holding device for holding the tissue or cartilage piece during the cutting of a desired slice, it is also possible—as shown with respect to the embodiments according to FIGS. 1a-c, 3a-d, and 4a,b—to provide a second holding device and, in the case of the embodiments of the invention not represented in the drawing, even a third holding device and, if necessary, even further holding devices. In the case of three or four holding devices, the holding devices are disposed relative to each other in the shape of a cross for ergonomic reasons.

Figure 1B:
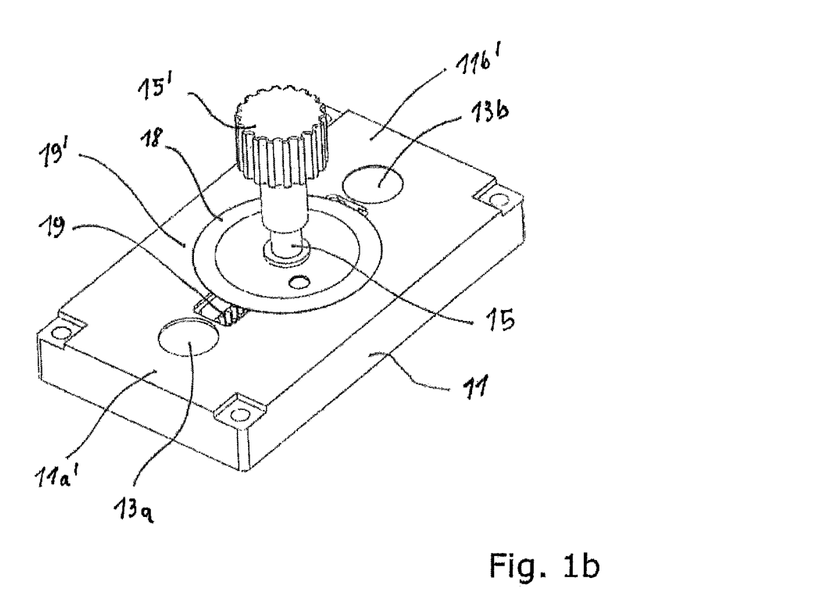
FIG. 1b shows the same as FIG. 1a, although with a rotating, circular cutting blade on the shaft.
Figure 1C:
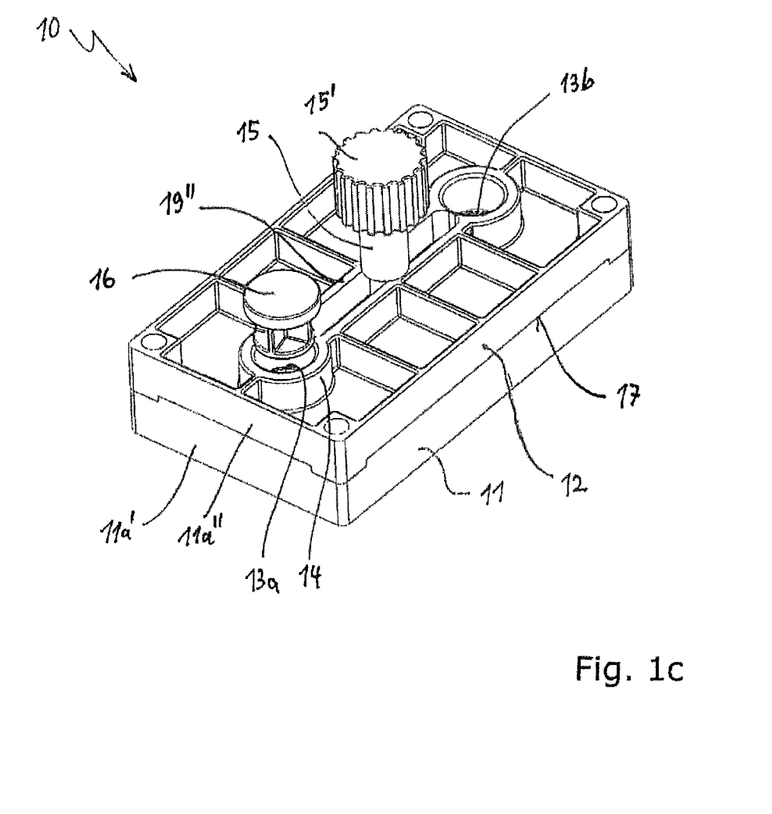
FIG. 1c shows the embodiment of FIG. 1b comprising a cover placed on the device body, and comprising a hold-down device in the first recess.

As in the embodiment according to FIGS. 1a-c, for example, adjoining the connecting section 19', opposite the first working section 11a', is a second working section 11b' or, as in the embodiments according to FIGS. 3a-d and 4a,b, also a third working section, each including the same shaped guide slot 17; 37; 47, wherein each working section 11a'; 11b' includes at least one recess 13a, 13b; 33a, 33b, 33c; 43a, 43b, 43c, and wherein the recesses 13a; 13b are disposed on a line or on a curved line in a plane extending in parallel to the plane of the guide slot 17; 37; 47.

Figure 5:
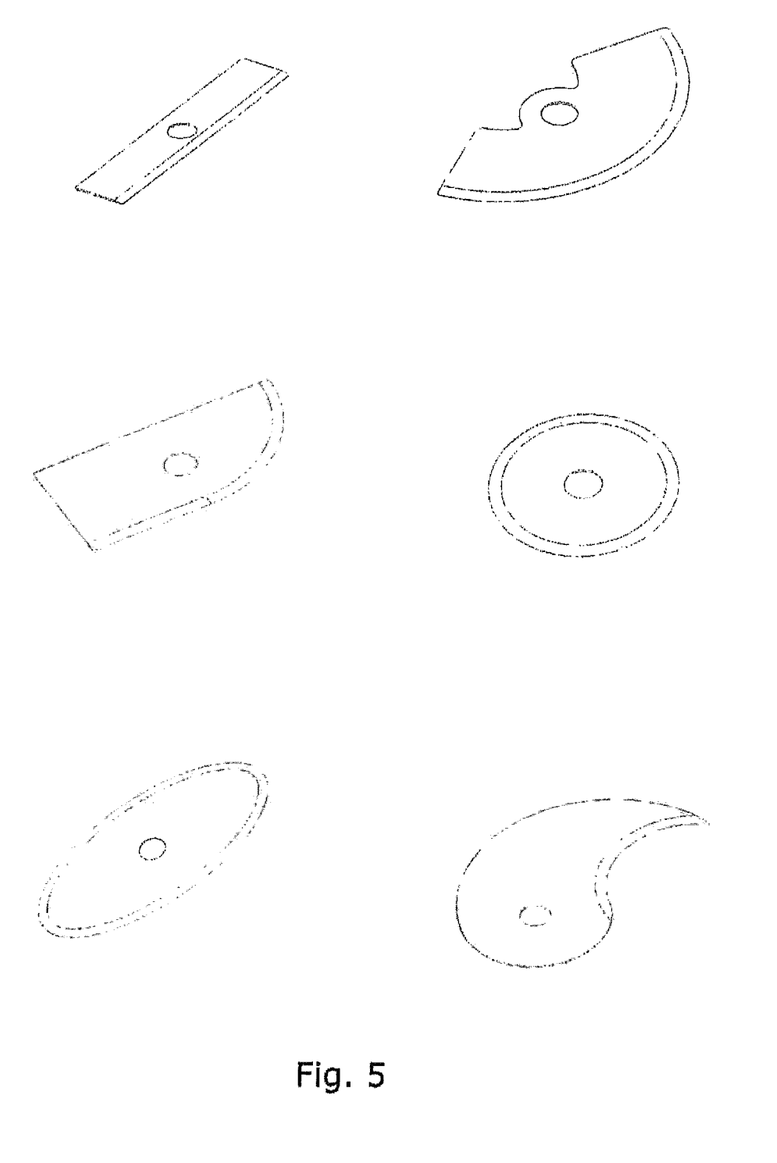
FIG. 5 shows a schematic view of various knife shapes.

The rotatable cutting blade 18; 28; 38; 48 of the cutting device 10; 30; 40 according to the invention can nave numerous different shapes, depending on the special intended use, for example an oval shape, or a crescent-shaped or bar-shaped form, or a circular shape, in particular on a circular segment, preferably on a quarter circle or semicircle. A small selection of such possible shapes of the rotatable cutting blade is represented in FIG. 5.

What is claimed is:

1. A medical cutting device for creating thin tissue or cartilage slices, comprising:
    a device body having a connecting section;
    a cover having a counterpart to the connecting section;
    a first holding device having a first working section comprising a first recess which is located on a top side of the device body, the recess being entirely or partially enclosed by a first limiting ridge, and
    a cutting blade;
    wherein the connecting section is directly, rigidly adjoined by the first working section,
    wherein the counterpart to the connecting section is directly, rigidly adjoined by a first pressure section,
    wherein, in an operating state of the cutting device, the first pressure section is disposed opposite the first recess in the first working section at an essentially uniform first distance $d_a$ defined by the geometric shape of the connecting section and the counterpart thereof, and therefore a guide slot extending between the first working section and the first pressure section remains free for the cutting blade,
    wherein a distance of the guide slot to the bottom surface of the first recess, which is defined by the distance $d_a$, defines a thickness, which can be achieved with the aid of the first holding device, of a slice to be created by means of the cutting device, and
    wherein the cutting blade is disposed within the guide slot and is rigidly connected to a rotatable shaft which is mounted so as to be rotatable about an axis of rotation extending perpendicularly to a plane of the guide slot and extends through a recess in the cover, perpendicularly to the plane of the guide slot.

2. The cutting device as claimed in claim 1, further comprising a hold-down device, by means ox which, in the operating state of the cutting device, tissue or cartilage material can be pressed onto the bottom surface of the first recess in order to create thin slices.

3. The cutting device as claimed in claim 2, wherein the hold-down device comprises a mechanical height limitation.

4. The cutting device as claimed in claim 2, wherein in the operating state of the cutting device, the hold-down device is configured to be manually pressed onto the tissue or cartilage material in order to create thin slices.

5. The cutting device as claimed in claim 2, wherein in the operating state of the cutting device, the hold-down device is configured to be automatically pressed onto the tissue or cartilage material, by means of spring force, in order to create thin slices.

6. The cutting device as claimed in claim 1, wherein the axis of rotation of the rotatable shaft is disposed in the cutting device in a stationary manner.

7. The cutting device as claimed in claim 1, wherein the axis of rotation of the rotatable shaft is disposed so as to be displaceable in the plane of the guide slot.

8. The cutting device as claimed in claim 7, wherein the axis of rotation of the rotatable shaft is disposed so as to be linearly displaceable in the plane of the guide slot.

9. The cutting device as claimed in claim 7, wherein the axis of rotation of the rotatable shaft is disposed so as to be displaceable on a curved path in the plane of the guide slot.

10. The cutting device as claimed in claim 7, wherein the rotatable shaft comprises a pinion which at least partially extends into the guide slot and, in the operating state of the cutting device, engages into a rack disposed in the connecting section.

11. The cutting device as claimed in claim 1, wherein a rotary knob is rigidly connected, outside the cover, to the rotatable shaft at an end of the rotatable shaft facing away from the cutting blade.

12. The cutting device as claimed in claim 1, wherein an engagement part for the motorized drive of the rotatable shaft is rigidly connected, outside the cover, to the rotatable shaft at an end of the rotatable shaft facing away from the cutting blade.

13. The cutting device as claimed claim 1, wherein the rotatable cutting blade has a form which is oval, crescent-shaped, bar-like or circular.

14. The cutting device as claimed in claim 1, wherein the holding device comprises several recesses which are situated under the guide slot in the operating state of the cutting device.

15. The cutting device as claimed in claim 14, wherein the recesses have highly different geometric designs with respect to their particular depth and/or with respect to their particular bottom surface in terms of shape and/or surface area and/or concave, flat, or convex design and/or with respect to their particular limiting ridge in terms of shape and/or size.

16. The cutting device as claimed in claim 1, wherein the connecting section is adjoined, opposite the first working section, by at least one second working section, and a third working section, each including the same shared guide slot, wherein each working section comprises at least one recess, and wherein the recesses are disposed on a line or on a curved line in a plane extending in parallel, to a plane of the guide slot.

17. The cutting device as claimed in claim 1, wherein the limiting ridge has a cross-section that is circular or oval or polygonal, in a plane extending in parallel to the plane of the guide slot.

* * * * *